United States Patent
Ex-Lubeskie et al.

(10) Patent No.: US 9,320,635 B2
(45) Date of Patent: Apr. 26, 2016

(54) SEMI-RIGID SHOULDER BRACES AND RELATED METHODS

(71) Applicant: Clemson University Research Foundation, Clemson, SC (US)

(72) Inventors: Chelsea Lea Ex-Lubeskie, Goose Creek, SC (US); Meredith Cole Donaldson, Westminster, SC (US); Riley Morgan Csernica, Mt. Pleasant, SC (US); Kaitlin Kathleen Grove, Roanoke, VA (US); Charles Alden Thigpen, Simpsonville, SC (US)

(73) Assignee: Clemson University Research Foundation, Clemson, SC (US)

( * ) Notice: Subject to any disclaimer, the term of this patent is extended or adjusted under 35 U.S.C. 154(b) by 197 days.

(21) Appl. No.: 13/971,410

(22) Filed: Aug. 20, 2013

(65) Prior Publication Data

US 2014/0058304 A1   Feb. 27, 2014

Related U.S. Application Data

(60) Provisional application No. 61/691,929, filed on Aug. 22, 2012.

(51) Int. Cl.
*A61F 5/00* (2006.01)
*A61F 5/01* (2006.01)
(Continued)

(52) U.S. Cl.
CPC ............. *A61F 5/0102* (2013.01); *A61F 5/3723* (2013.01); *A61L 15/14* (2013.01)

(58) Field of Classification Search
CPC ....... A61F 5/24; A61F 5/0118; A61F 5/3738; A61F 5/028; A61F 5/0102; A61F 5/3723; A61F 5/026; A61F 2005/0174; A61F 5/0123; A61F 5/055; A61F 5/34; A61F 5/3753; A61F 5/05841; A61F 5/04; A61F 5/0125; A61F 5/013; A61F 5/05808; A61F 2005/0179; A61F 5/022; A61F 2005/0134; A61F 2005/016; A61F 2005/0167; A61F 7/02; A41D 13/0153; A41D 13/05; A41D 31/0044; A41D 13/015; A42B 3/06; A42B 3/061; A42B 3/08; A42B 3/12; A43B 3/0063; A43B 5/145; A43B 7/20; A43B 7/28; A63B 2071/1233; A63B 2071/1241
USPC ....................... 602/4–5, 16–23; 128/878–879
See application file for complete search history.

(56) References Cited

U.S. PATENT DOCUMENTS

| 4,446,858 A | 5/1984 | Verter |
| 4,644,939 A | 2/1987 | Coleman |

(Continued)

OTHER PUBLICATIONS

International Search Report and Written Opinion for corresponding PCT Application No. PCT/US2013/055777, date of mailing Nov. 21, 2013.

(Continued)

*Primary Examiner* — Michael Brown
(74) *Attorney, Agent, or Firm* — Myers Bigel & Sibley, P.A.

(57) ABSTRACT

Shoulder braces for inhibiting secondary anterior shoulder dislocations that are configured to allow for a wide range of motion for mobility and stabilization, include a brace body with a single arm portion configured to reside about a shoulder of a user and a torso portion, a plurality of shoulder straps extending over the single arm portion shoulder, a substantially rigid thermoplastic insert releasably held by the arm portion of the brace body. The insert can have a user-specific custom shape that substantially conforms to shoulder anatomy of the shoulder of the user. The brace can also include at least one adjustable length laterally extending torso strap attached to the torso portion.

23 Claims, 9 Drawing Sheets

(51) Int. Cl.
*A61L 15/14* (2006.01)
*A61F 5/37* (2006.01)

(56) References Cited

U.S. PATENT DOCUMENTS

| | | | |
|---|---|---|---|
| 4,735,198 A * | 4/1988 | Sawa | 128/878 |
| 4,862,878 A | 9/1989 | Davison et al. | |
| 5,063,941 A | 11/1991 | White | |
| 5,188,587 A | 2/1993 | McGuire et al. | |
| 5,290,218 A * | 3/1994 | Kilbey | 602/4 |
| 5,405,312 A | 4/1995 | Jacobs | |
| 5,628,725 A | 5/1997 | Ostergard | |
| 6,106,493 A | 8/2000 | Rozell | |
| 6,146,346 A | 11/2000 | Godwin | |
| 6,306,111 B1 | 10/2001 | Dean | |
| 6,322,528 B1 | 11/2001 | Kania | |
| 6,332,528 B1 | 12/2001 | Rink | |
| 6,398,746 B2 * | 6/2002 | Bramlage et al. | 602/5 |
| 6,440,094 B1 * | 8/2002 | Maas | A61F 5/3738 2/44 |
| 7,081,101 B1 | 7/2006 | Sawa | |
| 7,207,963 B2 | 4/2007 | Kania et al. | |
| 7,255,679 B2 | 8/2007 | Kania et al. | |
| 7,320,669 B2 | 1/2008 | Campbell et al. | |
| 8,088,089 B2 | 1/2012 | Ciamillo et al. | |
| 8,287,478 B2 * | 10/2012 | Ostergard et al. | 602/20 |
| 2002/0010409 A1 * | 1/2002 | Bramlage et al. | 602/19 |
| 2002/0082537 A1 | 6/2002 | MacAllister | |
| 2003/0208146 A1 * | 11/2003 | Kania | 602/19 |
| 2005/0119595 A1 | 6/2005 | Kania et al. | |
| 2006/0167395 A1 | 7/2006 | Sawa | |
| 2007/0016121 A1 | 1/2007 | Kaminski et al. | |
| 2007/0106187 A1 * | 5/2007 | Campbell | A61F 5/3723 602/19 |
| 2008/0208092 A1 | 8/2008 | Sawa | |
| 2009/0149787 A1 | 6/2009 | Scott | |
| 2009/0149789 A1 | 6/2009 | Huang et al. | |
| 2011/0056004 A1 * | 3/2011 | Landi | A41D 13/015 2/459 |
| 2012/0022421 A1 | 1/2012 | Matthias | |
| 2012/0041352 A1 | 2/2012 | Ostergard et al. | |
| 2012/0101417 A1 | 4/2012 | Joseph | |

OTHER PUBLICATIONS

DonJoy Sully Shoulder Stabilizer, http://www.braceshop.com/productcart/pc/Saunders-Sully-Shoulder-S . . . , product example, 2 pages, date unknown but believed to be prior to the priority date of the current application, printed from the internet Aug. 6, 2012.

About Chesapeake Medical Products, http://www.chesapeakemedical.com/about.html, © 2011 Chesapeake Medical Products, Inc., 2 pages.

* cited by examiner

Chart showing average range of motion for test subjects (n=7) wearing no brace ☐ and Hi-Impact brace ▨

Average Range of Motion while wearing the Hi-Impact.
Red denotes external rotation above 90°

| Average Range of Motion with Hi-Impact | | | |
|---|---|---|---|
| Subject | Abduction | Rotation | Rotation at 90 deg |
| 1 | 105.00 | 98.00 | 86.00 |
| 2 | 142.00 | 88.00 | 88.00 |
| 3 | 137.00 | 74.00 | 8.00 |
| 4 | 132.00 | 85.00 | 74.00 |
| 5 | 133.00 | 74.00 | 80.00 |
| 6 | 158.00 | 93.00 | 110.00 |
| 7 | 135.00 | 76.00 | 105.00 |

Graphs showing average time for test subjects (n=7) to apply Hi-Impact v. trial

SEMI-RIGID SHOULDER BRACES AND RELATED METHODS

RELATED APPLICATIONS

This application claims the benefit of and priority to U.S. Provisional Application Ser. No. 61/691,929 filed Aug. 22, 2012, the contents of which are hereby incorporated by reference as if recited in full herein.

FIELD OF THE INVENTION

The present invention relates to shoulder braces.

BACKGROUND

Each year approximately 71,000 primary anterior shoulder dislocations occur in athletes playing high impact sports and can occur with other at-risk populations as well. See, Lauren Pearson, *Young Men and Elderly Women at Biggest Risk for Shoulder Dislocations*, Amer. Aca. of Orthopaedic Surgeons, Mar. 1, 2010. These individuals can be at increased risk for recurring dislocations. To lower this risk, patients are often prescribed one of two conventional shoulder orthotics, the SULLY brace or the SAWA brace, both manufactured by DonJoy Orthotics. However, the SULLY device is often thought to be too restrictive and uncomfortable and can impair athletic performance while the SAWA device, while more comfortable, may not provide enough stability to prevent recurrence of a dislocation.

SUMMARY OF EMBODIMENTS OF THE INVENTION

Embodiments of the present invention provide semi-rigid shoulder braces that provide stabilization of anterior glenohumeral ligaments without immobilizing the shoulder joint.

Shoulder braces for inhibiting secondary anterior shoulder dislocations are configured to allow for a wide range of motion while also providing shoulder joint stabilization.

Some embodiments are directed to shoulder braces that include a brace body with an arm portion configured to reside about a shoulder of a user and a torso portion. The braces include a plurality of shoulder straps extending over the single arm portion shoulder and a substantially rigid thermoplastic insert releasably held by the arm portion of the brace body. The insert has a user-specific custom shape that substantially conforms to a shoulder of the user. The brace also includes at least one adjustable length laterally extending torso strap attached to the torso portion.

The brace body can include an expandable, breathable compressive fabric.

The at least one torso strap can be a single strap that has an adjustable length and resides on only one side portion of the brace body. An opposing side portion can include two long edge portions that are releasably attachable.

The plurality of straps can include closely spaced straps that extend from a front upper portion of the brace body to a rear upper portion of the brace body and that are sized and configured to provide stabilization of ligaments. The straps have adjustable lengths.

The insert can substantially conform to an underlying gleno-humeral joint of the user/patient.

The brace can include an inner pocket that releasably holds the insert therein.

The insert can be held by a pocket attached to an internal surface of the brace body.

The insert can have a thickness between about 0.125 inches to about 0.25 inches.

The brace body can be formed from a stretchable compressive material that is configured to substantially conformably attach to the user and allow for resilient expansion to accommodate breathing.

Other embodiments are directed to methods of providing support to a user such as an athlete to inhibit secondary anterior shoulder dislocations. The methods include: (a) providing a shoulder brace with a plurality of shoulder straps residing over a single sleeve and a torso portion that has a substantially rigid insert that resides in a sleeve, the sleeve encasing an upper portion of a user's arm and compromised shoulder; (b) allowing a functional substantially full range of motion when the user wears the shoulder brace; and (c) providing compressive support to a glenohumeral joint of the compromised shoulder while also providing natural supportive function of shoulder ligaments when the user wears the shoulder brace.

Still other methods are directed to methods of treating a subject at risk for shoulder dislocation or needing support of a shoulder. The methods include: (a) providing a shoulder brace with a single arm portion and a torso portion; (b) molding a thermoplastic insert to conform to a shape of a humeral head of a shoulder of a patient; and (c) inserting the molded thermoplastic insert into the arm portion of the shoulder brace.

The providing step may optionally be carried out by providing at least one moldable insert in a kit with a compressible breathable fabric shoulder brace body. The shoulder brace can include a plurality of adjustable length shoulder straps that reside over the insert in the arm portion of the shoulder brace.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Other systems and/or methods according to embodiments of the invention will be or become apparent to one with skill in the art upon review of the following drawings and detailed description. It is intended that all such additional systems, methods, and/or devices be included within this description, be within the scope of the present invention, and be protected by the accompanying claims.

BRIEF DESCRIPTION OF THE DRAWINGS

Other features of the present invention will be more readily understood from the following detailed description of exemplary embodiments thereof when read in conjunction with the accompanying drawings.

DETAILED DESCRIPTION OF EMBODIMENTS OF THE INVENTION

Figure 1A:
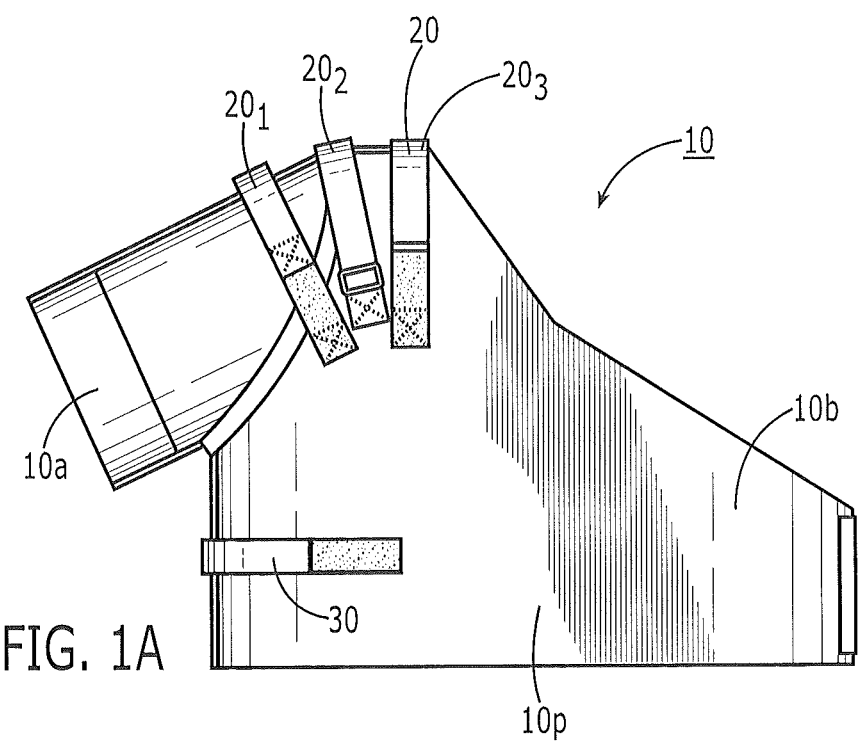
FIG. 1A is a front view of a right shoulder brace according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise. One or more features shown and discussed with respect to one embodiment may be included in another embodiment even if not explicitly described or shown with another embodiment.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The term "about" means that the recited number or value can vary by +/−20%.

Embodiments of the invention are particularly suitable for human uses and/or some veterinary uses.

Figure 1B:
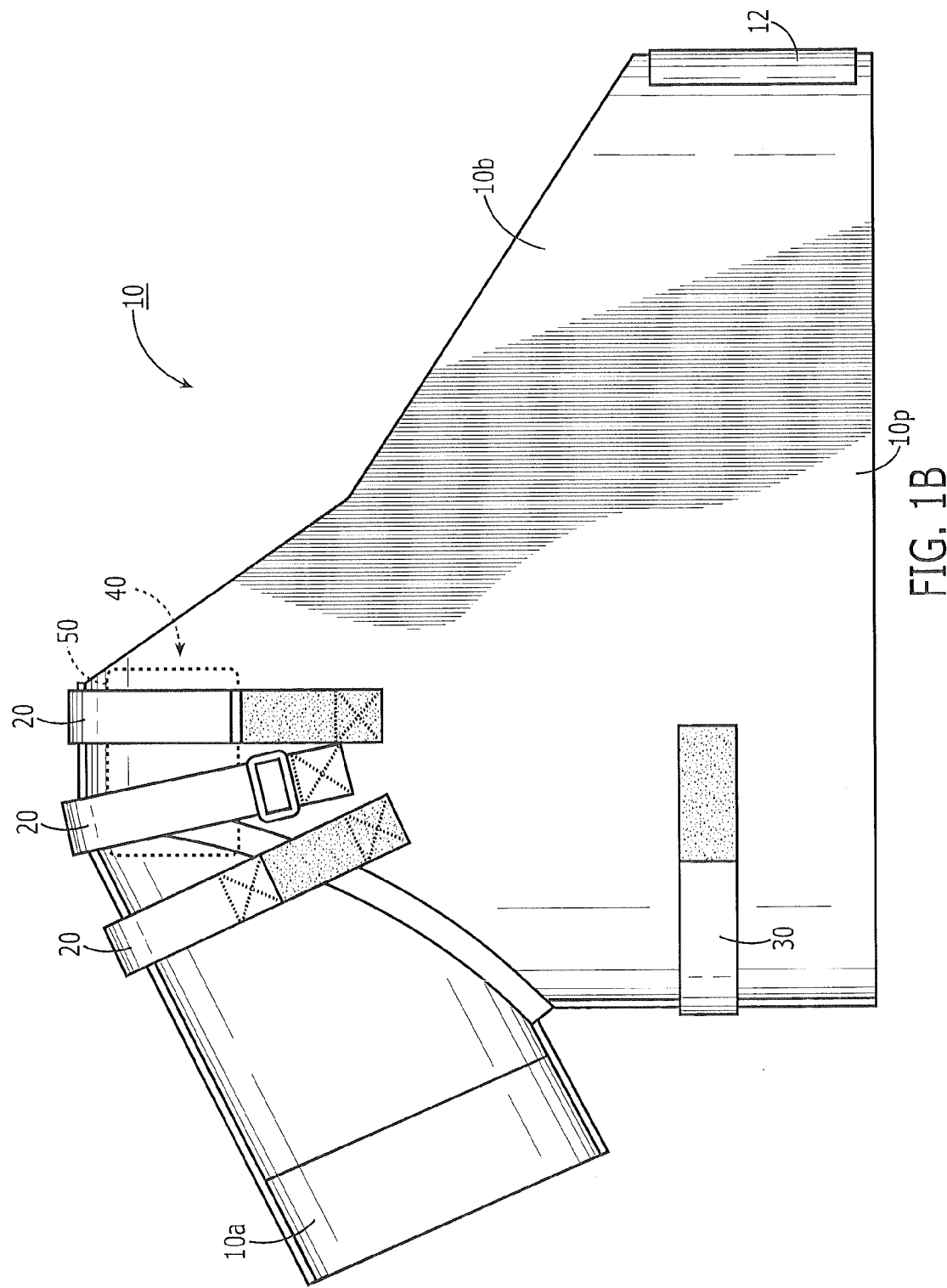
FIG. 1B is an enlarged view of the brace shown in FIG. 1A illustrating a location of an (internal) insert according to embodiments of the present invention.

Turning now to the figures, FIGS. 1A and 1B illustrate an example of a shoulder brace 10 according to embodiments of the present invention. The brace 10 can be lightweight such as under about 1 pound, including, for example, about 0.75 pounds, about 0.5 pounds (about 170 grams), about 0.25 pounds or even less. The brace 10 includes a brace body 10*b* that holds an insert 40 over the anterior glenoid-humeral joint. The insert 40 is typically a semi-rigid or rigid thermoplastic insert. The brace body 10*b* can comprise a flexible (stretchable) compressive material, typically a material that is "breathable" for user comfort. The brace body 10*b* includes a single arm portion 10*a* that fits onto a user's arm and a torso portion 10*p*. The torso portion 10*p* can include at least one longitudinally extending side 11 with longitudinally extending edge portions 12 that are releasably attachable together to allow a user to relatively easily take the brace on and off. VELCRO® or hook and loop attachments can be used. In other embodiments, buckles, buttons, zippers or snaps (alone or in any combination) can be used.

Suitable breathable fabrics include neoprene or other materials that have "stretch" or elastomeric fibers such as spandex. LYCRA® is an example of a spandex stretch fiber. Other stretch fibers may also be suitable. Such stretch fibers may include, but are not limited to, fibers presently classified in the polyester textile label classification of the U.S. Federal Trade Commission, but under which a new subclass of "elasterell-p" has been proposed; these, may also be suitable as stretch fibers as the are described as inherently elastic, bicomponent textile fibers consisting of two substantially different forms of polyester fibers (DuPont's version of this fiber is referred to as "T400").

In other embodiments, the brace body 10*b* can include a zipper that attaches the two edge portions 12. The two edge portions 12 may be on the side or may reside in a center or other user accessible portion of the torso portion 10*p* brace body to allow for easy donning and removal.

Figure 3:
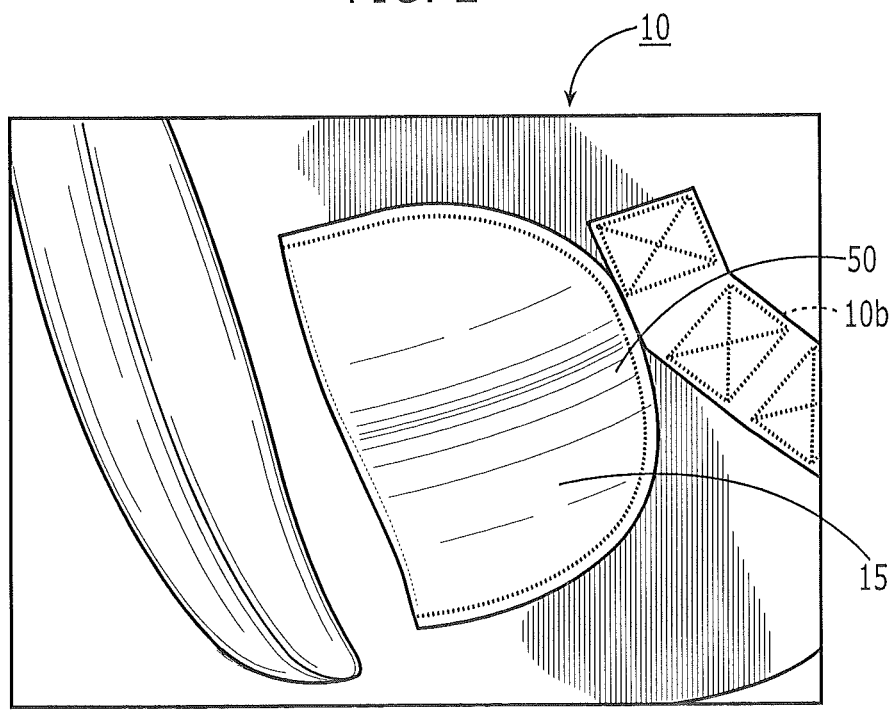
FIG. 3 is a top view of an exemplary insert pocket on a shoulder portion of the device shown in FIG. 1A according to embodiments of the present invention.

The brace body 10*b* can include portions that are compressive and portions that are not. The brace body 10*b* can be a monolithic single layer or multi-layer configuration. The brace body 10*b* can include a plurality of different materials, defining different portions of the brace body. In some embodiments, the brace body 10*b* includes a pocket 15 for an insert 40 (FIGS. 3, 4).

Figure 2:
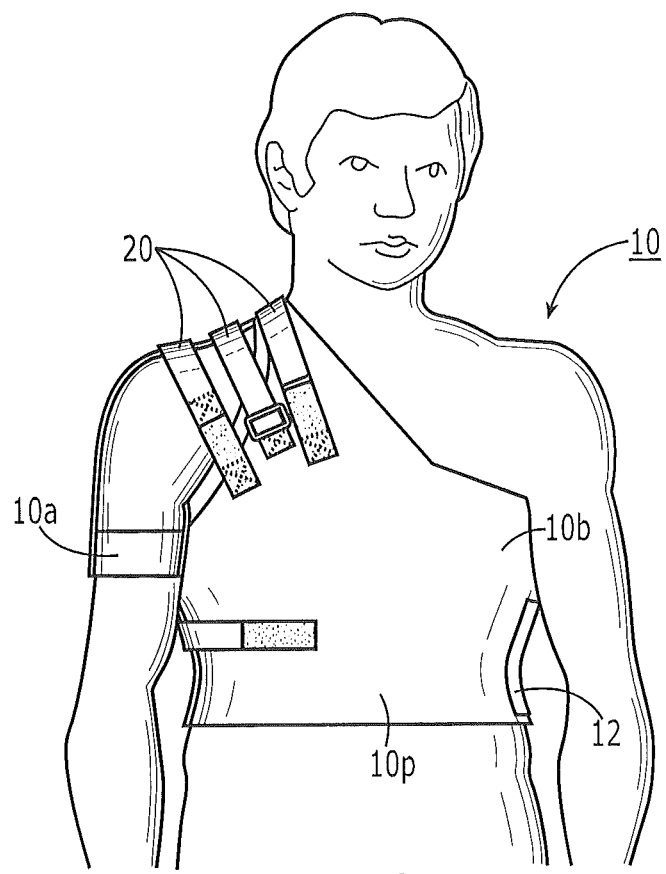
FIG. 2 is a front view of the device shown in FIG. 1A, shown on a patient/user according to embodiments of the present invention.

As shown in FIGS. 1A, 1B and 2, the brace 10 includes a plurality of adjustable length shoulder straps 20 that extend over the shoulder. The straps 20 can allow a user or clinician to control the tightness of the brace 10 to provide adequate shoulder support while allowing an average of about 110 degrees abduction and about 90 degrees external rotation (see FIG. 6). The brace 10 can be configured to control a range of motion so that simultaneous abduction of greater than 90 degrees and external rotation of greater than 90 degrees is inhibited. The plurality of shoulder straps 20 can include at least three straps (shown as three straps $20_1$, $20_2$, $20_3$) although two or more than three straps 20 may be used. The (three) shoulder straps 20 can be oriented across the shoulder to mimic the natural function of glenohumeral ligaments. It is contemplated that the brace can provide up to about 770 N of (dynamic) support, typically between about 600 N to about 770 N of support, although other support ranges may be provided.

The brace 10 can also include at least one laterally extending adjustable torso strap 30 that resides proximate to but under the arm at an upper to medial portion of the torso. The at least one torso strap 30 can be a single strap or more than one strap. Where multiple torso straps 30 are used, they can reside on a single side of the brace, typically on the same side as the shoulder straps 20 or on different sides (or even front or back). The torso strap 30 can be used to tighten the brace to conform to the user while allowing for resilient chest expansion during breathing. The torso portion 10*p* of the brace 10 with the torso strap 30 can allow for outward expansion of up to about three inches.

The pocket 15 can be an externally accessible pocket formed in the compressible material of the brace body 10*b*. However, as shown in FIG. 3, the pocket 15 can be formed using an inner layer of material 50 (such as nylon) that is attached to an anterior (internal surface or side) of the arm portion 10*a* of the brace body 10. The term "pocket" is used broadly and refers to any compartment that (detachably) holds the insert 40 and is not required to have a continuous outer surface. The pocket 15 can be sewn or chemically (e.g., adhesively) attached to the primary body of the brace or formed in other manners as will be known by those of skill in the art. The pocket 15 can be an interior nylon pocket configured with one open portion that can be releasably attached or sized to retain the insert but also allow the insert 40 to be removed for washing the brace body 10*b* and/or to be inserted post-formation to substantially conform to the patient's anatomical shoulder shape. In other embodiments, the insert 40 can comprise integral mounting components such as a surface with VELCRO® type fasteners, fabric hooks or loops that attach to an underlying or overlying surface of the brace body with the cooperating loops or hooks, adhesives or other mounting configurations that do not require a pocket.

Figure 4A:
FIG. 4A is a side view of an insert before being formed with a custom user shoulder shape.
Figure 4B:
FIG. 4B is a side view of the insert shown in FIG. 4A after formed to have a custom shape that confirms to a user's shoulder according to embodiments of the present invention.
Figure 9A:
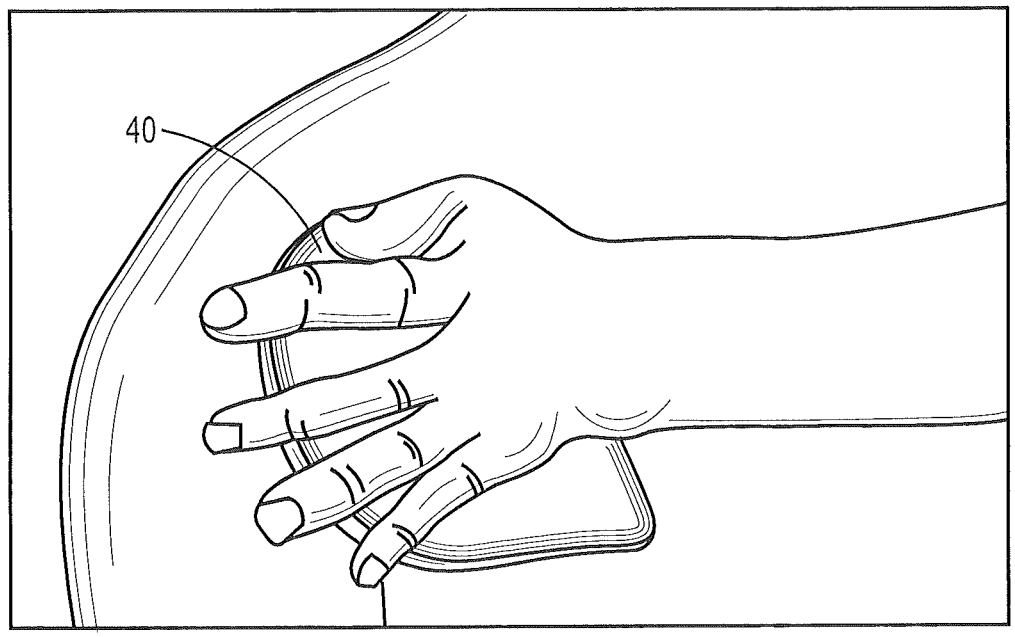
FIG. 9A is a front perspective view of a clinician or other person molding the insert to a user's anterior glenoid humeral joint shape according to embodiments of the present invention.
Figure 9B:
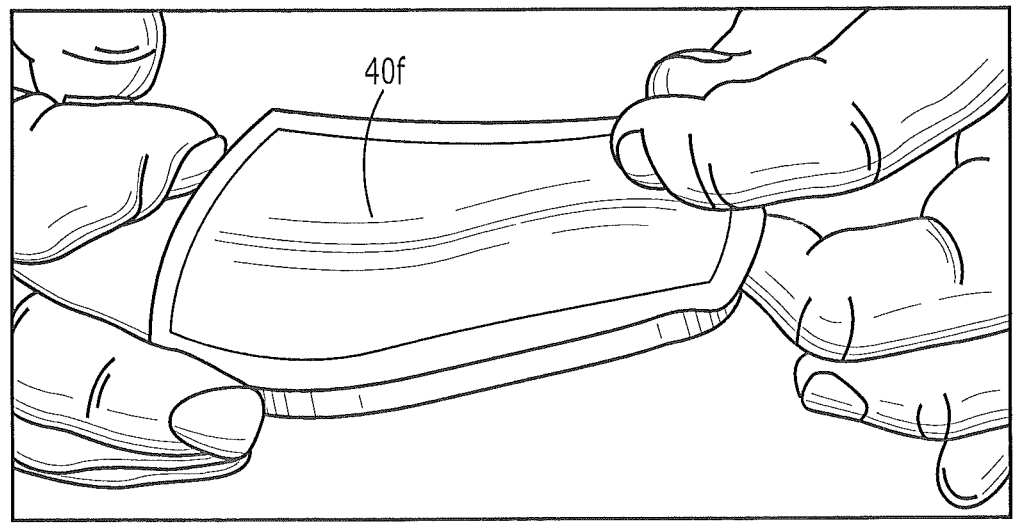
FIG. 9B is a top perspective view of the insert shown in FIG. 9A in a custom form shape ready for attachment to the brace according to embodiments of the present invention.

As shown in FIG. 4A, the insert 40 can be provided as a planar body that is custom shaped to a user's shoulder prior to use of the brace. FIG. 4B illustrates a post-molded insert 40*f*. FIG. 9A illustrates the insert 40 being molded to conform to a patient's shape at forward portion of the shoulder (below the top) at/over the glenohumeral joint. Typically, the insert 40 resides over the (anterior) glenohumeral joint and does not extend over the top of the shoulder or down the sleeve of the brace 10. FIG. 9B illustrates the post-mold shape 40*f* ready for insertion into the pocket of the brace 10. In FIG. 9B, the insert 40 is shown upside down and in use it is rotated about 90 degrees upward with the cavity facing the shoulder of the user. The insert 40 is typically a thermoplastic insert of suitable size and shape, e.g., between about 0.125 inches to about 0.50 inches thick, typically between about 0.125 to about 0.25 inches thick. The insert 40 can be a low-temperature thermoplastic material of synthetic or natural material, such as polymers and/or rubbers. In some embodiments the thermoplastic material can comprise MARQUE EASY™ thermoplastic material from Chesapeake Medical Products, Inc. In use, the insert 40 can be substantially rigid while the brace body 10*b* is flexible allowing for mobility of the joint with stabilization.

Although not required, the insert 40 may optionally include a gel or neoprene material that provides padding for additional comfort.

The insert 40 can be heated to between about 65° C.-70° C. (150° F.-160° F.) for a about 1 minute and allows for a work time of between about 3-5 min to form the desired shape. The area of the insert 40 may vary depending on size of the brace (e.g., XS, S, M, L, XL and the like) but typically has an area that is between about 10 in$^2$ to about 20 in$^2$. In particular embodiments, the insert 40 can be about 0.125 inch thick with a 3×5 inch substantially oval shape. In other embodiments, other geometric shapes such as polygons can be used. In some embodiments, the insert 40 can be a custom-fitted (low temperature) thermoplastic insert that substantially conforms to a user's shoulder (external anatomy over a humeral head) to increase support and proprioception and can be easily inserted and removed from its designated pocket on an interior facing side the brace 10.

The insert 40 cooperates with the brace body 10b providing a semi-rigid device that provides support for weakened anterior shoulder ligaments as a result of dislocations.

While particularly suitable for athletes experiencing or at-risk for recurring anterior shoulder dislocations, the braces 10 are also suitable for anyone desiring additional shoulder support.

Figure 5A:
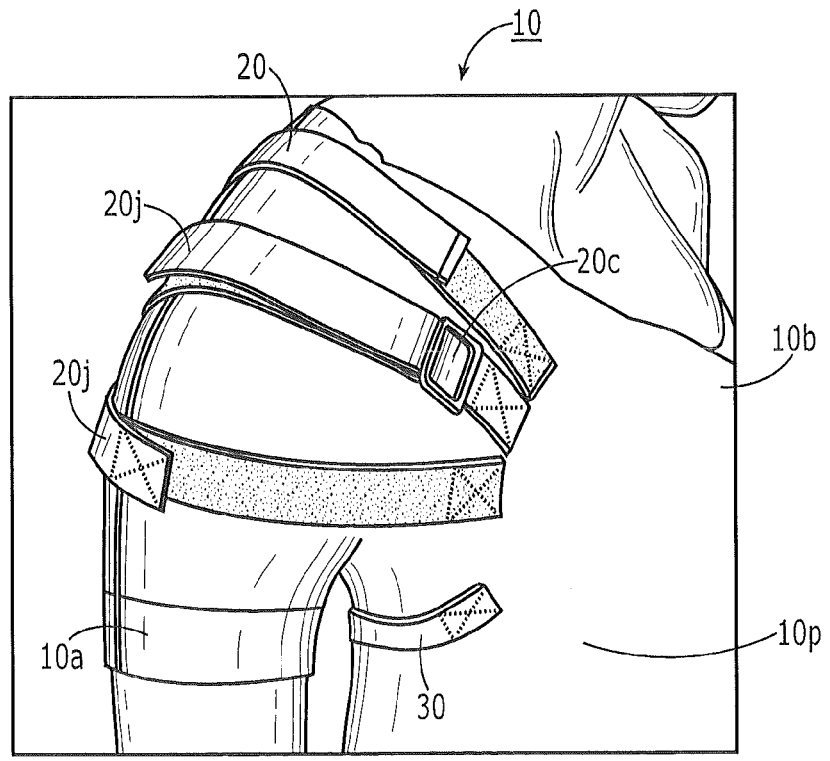
FIG. 5A is an anterior perspective view of the brace shown in FIG. 1A.
Figure 5B:
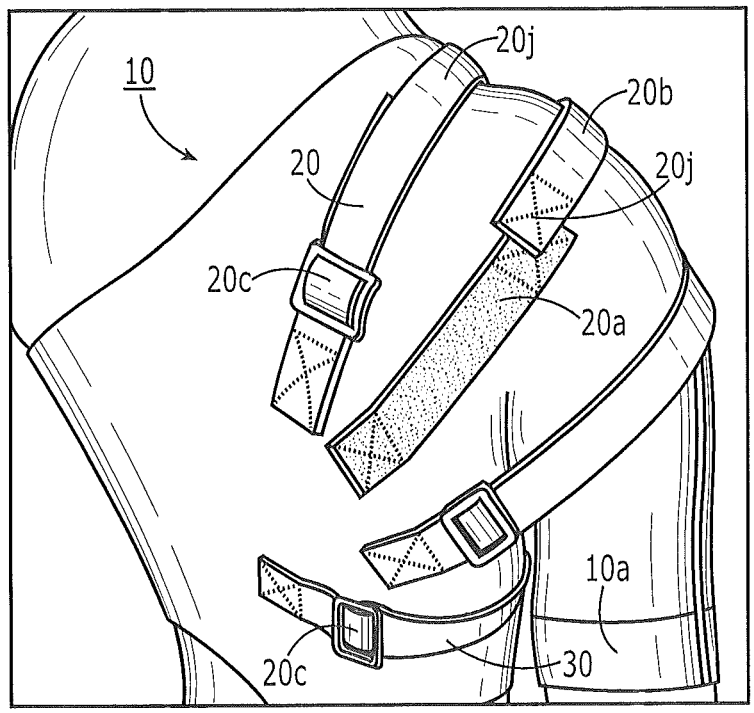
FIG. 5B is a posterior perspective view of the brace shown in FIG. 1A.

As shown in FIGS. 5A and 5B, the shoulder straps 20 (and torso strap 30) can comprise nylon and may include one side that has adjustable length with corresponding pairs of strap legs 20a, 20b attachable at a joint 20j by hook and loop type attachment. The straps 20 can be configured so that a buckle (allowing for adjustable length of one side of the strap) location 20c is on the first end 20a on one strap and on the second end 20b on the adjacent strap. In some embodiments, other releasable attachment members can be used in lieu of or with the hooks and loops and other adjustable length members can be used in lieu of buckles. The straps 20 can apply pressure against the underlying insert 40 to keep the insert in position and/or apply stabilizing forces against the humeral head of the shoulder.

The brace 10 can restrict abduction and external rotation of the shoulder joint to about 90 degrees combined abduction and external rotation, which can provide stabilization in the area of the anterior glenohumeral ligaments and provide sufficient force to keep the shoulder in place without immobilizing the joint.

The brace body 10b can comprise a breathable neoprene fabric which is lightweight and has a low profile fit allowing it to fit under athletic clothing and/or padding such as those often worn by athletes.

FIGS. 1A, 1B, 2, 5A and 5B show a right shoulder brace 10. The left shoulder brace is similarly configured but with the arm 10a on the left side of the brace body 10b.

The brace 10 can be provided in a range of sizes to accommodate different size users, e.g., extra small (XS), small, medium, large, extra large and even larger (typically 2XL and 3XL). The brace 10 can be provided in pediatric and adult size ranges and/or female to male configurations. Female configurations may have a different torso shape or size. Female adult sizes may be provided in a range of cup and chest sizes for better form fit.

Figure 6A:
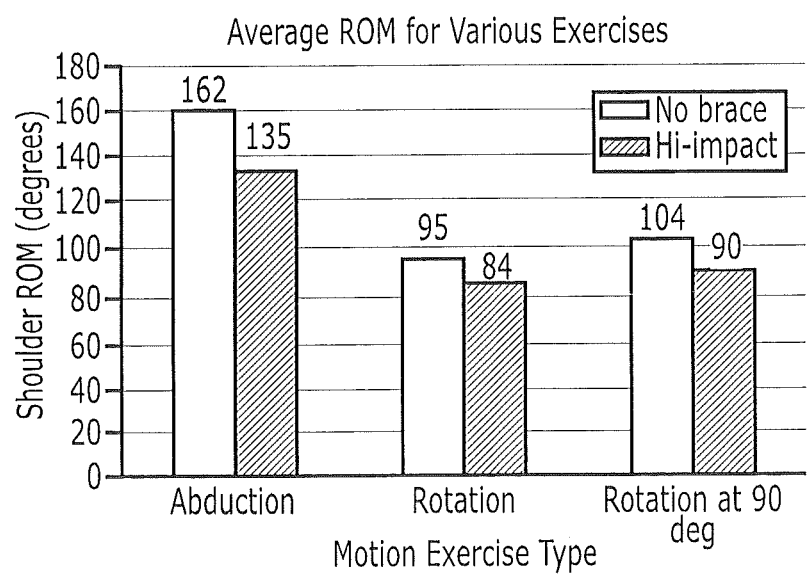
FIG. 6A is a graph of shoulder range of motion (ROM) in degrees (average) by motion exercise type allowed by no brace versus the (high-impact) semi-rigid shoulder brace shown in FIG. 1A (n=7) according to embodiments of the present invention.

FIG. 6A is graph that shows the relative mobility allowed by the brace 10 through a wide range of motion for different exercise types allowing for a user to participate in most sport activities, substantially comparable to people not wearing a brace, when wearing the braces 10.

Figures 6B, 7:
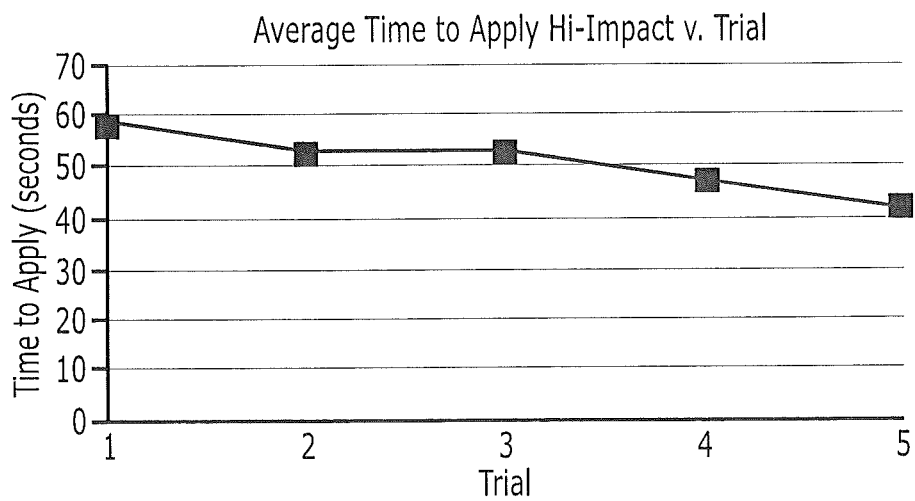
FIG. 6B is a table that shows average range of motion for subjects (n=7) using the brace shown in FIG. 1A according to embodiments of the present invention.
FIG. 7 is a graph of time (average) for a user to self-attach the high-impact, semi-rigid brace for five different trials according to embodiments of the present invention.

FIG. 6B is a table of average range of motion of different users wearing the brace. The braces 10 can reduce the average range of motion for all subjects in all natural movements. Each subject completed a series of range of motion tests while wearing the brace 10 shown in FIGS. 1A/1B with the custom formed insert 40. Comparison tests were then performed to find each subject's baseline. The range of motion for adduction was tested using a goniometer to measure deflection of the arm from 0 degrees at rest by the side to the maximum in-plane deflection. The amount of external rotation was measured with the humerus hanging at the side and the elbow bent 90 degrees, parallel to the ground. The amount of external rotation was measured with the humerus held at 90 degrees adduction, and the forearm at 90 degrees to the humerus. The motions were repeated three times and the average deflection was calculated. The brace 10 can reduce the average range of motion for most users to 90 degrees showing the ability of the brace to support and improve stability during these motions in the glenohumeral joint.

In some embodiments, the brace 10 is configured to allow for relatively quick donning and removal (e.g., on and off) times by a person without requiring any assistance for most users. This convenient self-assembly and removal can promote compliance and potentially avoid recurrence of shoulder dislocations. FIG. 7 illustrates that users can easily self-attach the brace 10 in about 1 minute or less.

Figure 8:
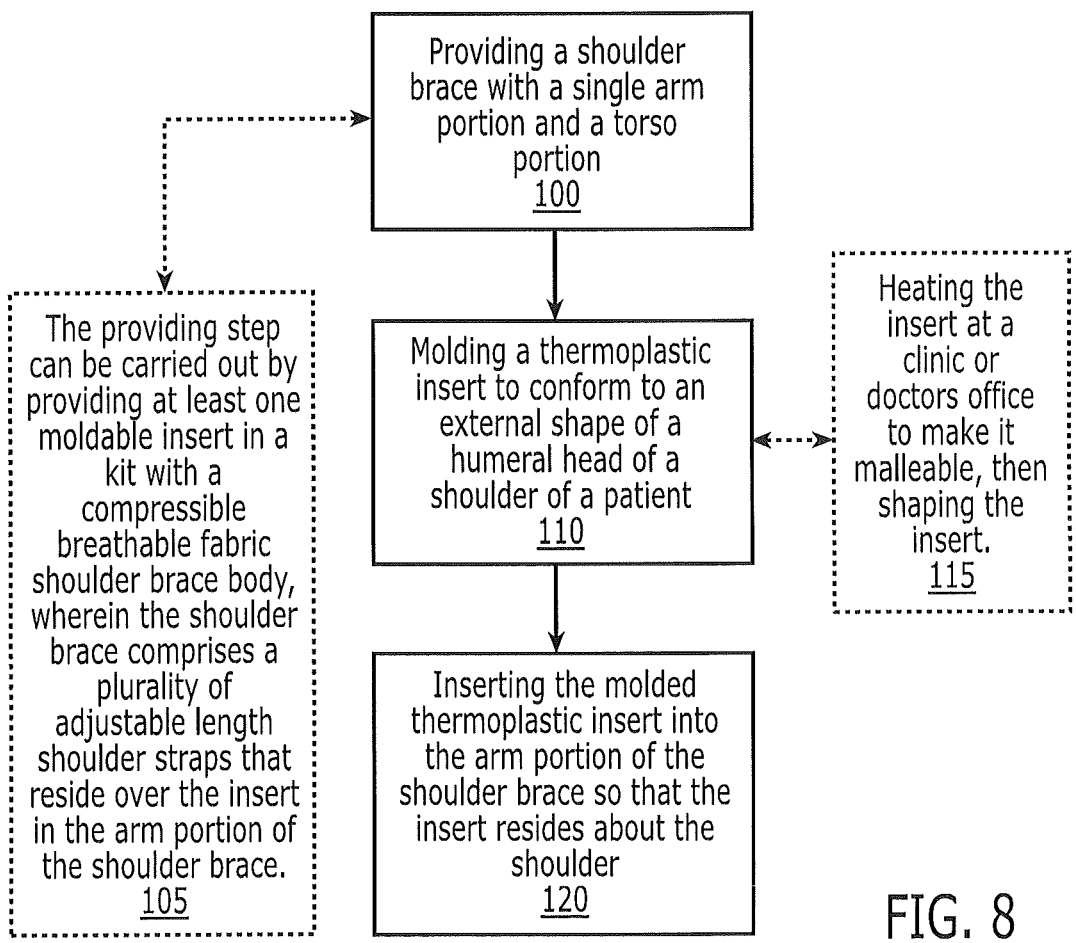
FIG. 8 is a flow chart of exemplary operations that can be used to carry out embodiments of the present invention.

FIG. 8 illustrates exemplary steps or operations that can be used to treat a subject (e.g., an athlete) at risk for shoulder dislocation or needing support of a shoulder. A shoulder brace with an arm portion (typically a single arm portion) and a torso portion is provided (block 100). A thermoplastic insert can be molded to conform to a shape of a humeral head of a shoulder of a patient (block 110). The molded thermoplastic insert can be inserted into the arm portion of the shoulder brace so that the insert resides about the shoulder (block 120).

The providing step can be carried out by providing at least one moldable insert in a kit with a compressible breathable fabric shoulder brace body. The shoulder brace can include a plurality of adjustable length shoulder straps that reside over the insert in the arm portion of the shoulder brace and the method can include adjusting the straps to provide desired support and compressive strength of the insert against the shoulder (block 105).

The insert can be heated at a clinic or doctor's office to make it malleable, then the insert can be shaped for the molding step (block 115). The brace can be provided in a package with a training manual, template or instruction sheet and/or a web link to a video that shows how to mold the insert. The insert may also come with indicia of orientation for placement into the brace (e.g., pocket) such as "up" or "down" or "faces in" or "faces out" surface markings (arrows, icons or images may also be used).

Figure 10A:
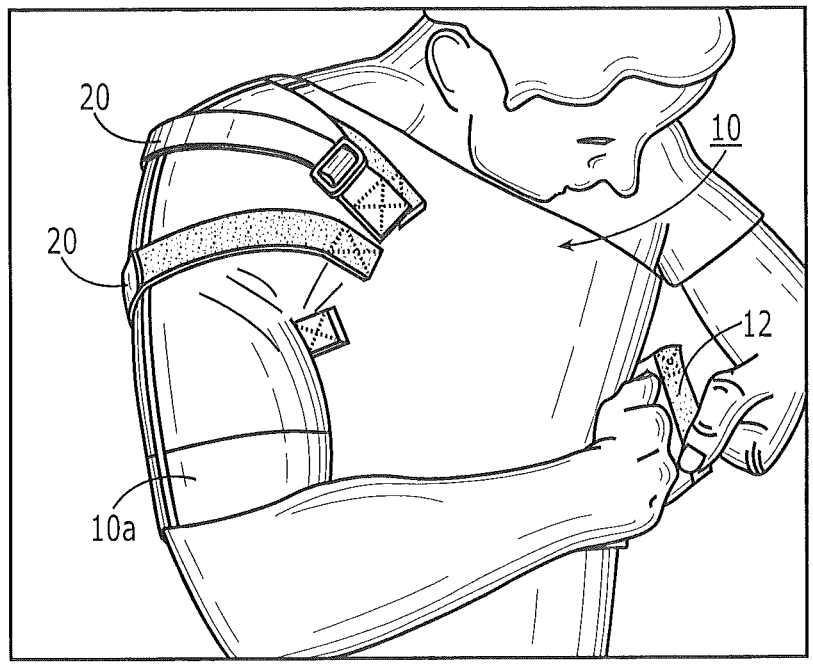
FIGS. 10A and 10B are sequential front perspective views of a user self-applying (donning) the brace according to some embodiments of the present invention.
Figure 10B:
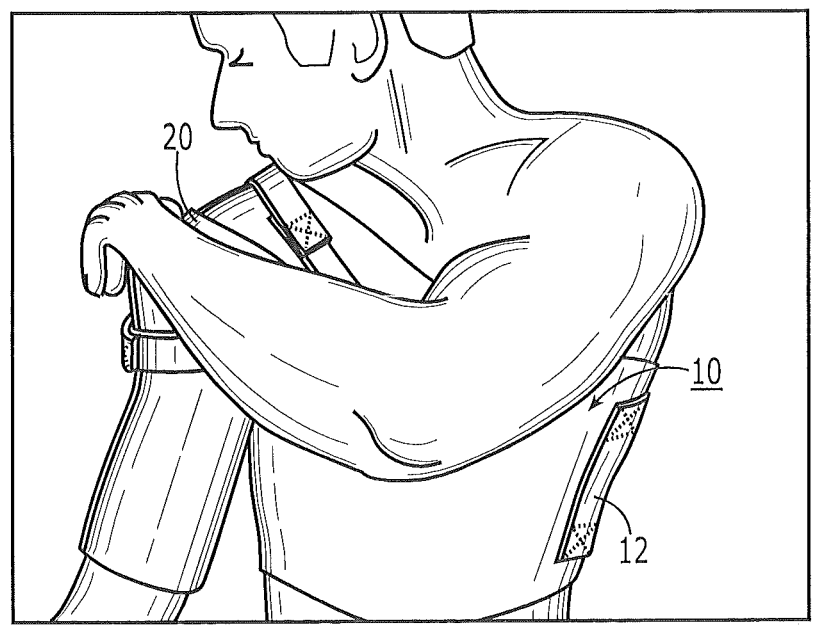

FIGS. 10A and 10B illustrate a patient/user self-applying (donning) the brace 10. A user slips an arm through the sleeve (with the straps 20 loose), pulls the body 10b closed on the opposing side and attaches the side 12. The user then tightens the straps 20 and strap 30 as needed.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

That which is claimed:

1. A shoulder brace, comprising:
   a brace body with an arm portion configured to reside about a shoulder of a user and a torso portion;
   a plurality of shoulder straps extending over the arm portion from a front upper portion to a back upper portion of the brace body; and
   a substantially rigid thermoplastic insert releasably held by the arm portion of the brace body, wherein the insert has a user specific custom shape that substantially conforms to a glenohumeral joint over a humeral head of a shoulder of the user,
   wherein the thermoplastic insert is malleable above a defined temperature but retains the custom shape at room temperature, wherein the thermoplastic insert has a thickness that is in a range of about 0.125 inches to about 0.5 inches, and an area in a range of about 10 in$^2$ to about 20 in$^2$, and wherein at least one of the shoulder straps has an adjustable length and resides over at least a portion of the thermoplastic insert.

2. The shoulder brace of claim 1, wherein the brace body comprises an expandable breathable compressive fabric.

3. The shoulder brace of claim 1, wherein the torso portion comprises a single torso strap that has an adjustable length.

4. The shoulder brace of claim 1, wherein the plurality of shoulder straps comprise a plurality of closely spaced straps that extend from a front upper portion of the brace body to a rear upper portion of the brace body and that are sized and configured to provide stabilization of glenohumeral ligaments, and wherein all the shoulder straps have adjustable lengths.

5. The shoulder brace of claim 1, wherein the brace body arm portion comprises an inner pocket that releasably holds the insert therein.

6. The shoulder brace of claim 1, wherein the insert is held by a pocket attached to an internal surface of the brace body.

7. The shoulder brace of claim 1, wherein the torso portion comprises a stretchable compressive material that is configured to substantially conformably attach to the user and allow for resilient expansion to accommodate breathing.

8. The shoulder brace of claim 1, wherein the insert is malleable in a temperature range of 65 degrees Celsius to 70 degrees Celsius, and wherein the brace provides stabilization of anterior glenohumeral ligaments without immobilizing the shoulder joint and inhibits simultaneous abduction of greater than 90 degrees and external rotation of greater than 90 degrees.

9. A method of providing support to a user such as an athlete to inhibit secondary anterior shoulder dislocations, comprising:
providing a shoulder brace with a plurality of shoulder straps residing over a single sleeve and a torso portion, wherein the brace has a substantially rigid thermoplastic insert that resides in a sleeve, the sleeve encasing an upper portion of a user's arm and compromised shoulder;
allowing a functional substantially full range of motion when the user wears the shoulder brace; and
providing compressive support to a glenohumeral joint of the compromised shoulder while also providing natural supportive function of shoulder ligaments when the user wears the shoulder brace.

10. A method of treating a subject at risk for shoulder dislocation or needing support of a shoulder, comprising:
providing a shoulder brace;
providing a thermoplastic member having a first shape at room temperature;
heating the thermoplastic member to a malleable temperature;
pressing the thermoplastic member against a humeral head of a shoulder of a patient to cause the thermoplastic member to take on and retain at room temperature a custom three dimensional shape with contours conforming to a shape of the humeral head of the patient; and
placing the custom shape thermoplastic member so that the thermoplastic member resides over an anterior glenoid-humeral joint of the shoulder.

11. The method of claim 10, wherein the providing step is carried out by providing the thermoplastic member in a kit with the shoulder brace, wherein the shoulder brace comprises a plurality of adjustable length straps that, in use, cooperate with the custom shape thermoplastic member.

12. The shoulder brace of claim 1, wherein the insert is configured to conform to and reside over an anterior glenoid-humeral joint of the shoulder.

13. The shoulder brace of claim 1, wherein the insert is a thermoplastic insert that is malleable at a temperature between about 65 degrees Celsius and 70 degrees Celsius.

14. The shoulder brace of claim 13, wherein the thermoplastic insert is manually malleable for between 3-5 minutes when heated to a temperature in a range of about 65 degrees Celsius to about 70 degrees Celsius for about 1 minute.

15. The shoulder brace of claim 1, further comprising at least one adjustable length laterally extending torso strap.

16. The shoulder brace of claim 1, wherein the insert resides under a top of the shoulder and over an entire humeral head.

17. A shoulder brace, comprising:
at least one strap that extends over a shoulder of a user; and
a substantially rigid thermoplastic member in communication with the at least one strap, wherein the thermoplastic member has a user-specific custom shape that has a primary surface with an area having a fixed three dimensional shape with contours that conform to a glenohumeral joint over a humeral head of a shoulder of the user, wherein the thermoplastic member is malleable above a defined temperature but retains the custom shape at room temperature, and wherein the at least one strap cooperates with the thermoplastic member to provide shoulder support while (a) allowing an average range of motion of about 110 degrees abduction and about 90 degrees external rotation and (b) inhibiting simultaneous abduction of greater than 90 degrees and external rotation of greater than 90 degrees.

18. A shoulder brace, comprising:
at least one strap that extends over a shoulder of a user; and
a substantially rigid thermoplastic member in communication with the at least one strap, wherein the thermoplastic member has a user-specific custom shape that substantially conforms to a glenohumeral joint over a humeral head of a shoulder of the user, wherein the thermoplastic member is malleable above a defined temperature but retains the custom shape at room temperature, wherein the thermoplastic member has a thickness between about 0.125 inches to about 0.25 inches, and an area in a range of about 10 in$^2$ to about 20 in$^2$, and wherein the at least one strap has an adjustable length and resides over at least a portion of the thermoplastic member.

19. The shoulder brace of claim 17, wherein the thermoplastic member is manually malleable for between 3-5 minutes when heated to a temperature that is in a range of about 65 degrees Celsius to about 70 degrees Celsius for about 1 minute.

20. The shoulder brace of claim 17, wherein the thermoplastic member resides under a top of the shoulder and the custom shape conforms to an anterior gleno-humeral joint of the shoulder.

21. A method of providing support to a user such as an athlete to inhibit secondary anterior shoulder dislocations, comprising:
providing a shoulder brace with at least one shoulder strap in communication with a thermoplastic member that has a user-specific custom three-dimensional shape with contours that conform to a glenohumeral joint, wherein the custom shape is fixed at room temperature;
positioning the thermoplastic member to reside over a gleno-humeral joint to engage a compromised shoulder while in cooperating engagement with the at least one shoulder strap;
allowing a functional substantially full range of motion when the user wears the shoulder brace; and providing compressive support to a glenohumeral joint of the compromised shoulder while also providing natural supportive function of shoulder ligaments when the user wears the shoulder brace.

22. The method of claim 21, wherein the allowing and providing steps are carried out by the shoulder brace so that the at least one strap cooperates with the thermoplastic member to provide shoulder support while (a) allowing an average range of motion of about 110 degrees abduction and about 90 degrees external rotation and (b) inhibiting simultaneous abduction of greater than 90 degrees and external rotation of greater than 90 degrees.

23. The method of claim 21, wherein the allowed range of motion is carried out to restrict external rotation of the joint to about 90 degrees thereby providing stabilization of the anterior glenohumeral ligaments while providing sufficient force to retain the shoulder in place without immobilizing the shoulder joint.

* * * * *